United States Patent [19]

Soyama et al.

[11] Patent Number: 5,225,195
[45] Date of Patent: Jul. 6, 1993

[54] SOLVENT TYPE NAIL ENAMEL COMPOSITION

[75] Inventors: Yoshikazu Soyama; Yoshiyuki Ogusu; Toshihide Ikeda, all of Yokohama; Yoshio Okamura, Takasaki; Teruo Kurosaki, Matsudo, all of Japan

[73] Assignee: Shiseido Company Ltd., Tokyo, Japan

[21] Appl. No.: 619,143

[22] Filed: Nov. 28, 1990

[30] Foreign Application Priority Data

Nov. 29, 1989 [JP] Japan .................................. 1-309856
Mar. 28, 1990 [JP] Japan .................................. 2-79658

[51] Int. Cl.$^5$ .............................................. A61K 6/00
[52] U.S. Cl. ...................................... 424/401; 424/61
[58] Field of Search ................................. 424/401, 61

[56] References Cited

U.S. PATENT DOCUMENTS 4,229,227 10/1980 Ikeda et al. ..................... 106/181

FOREIGN PATENT DOCUMENTS 1201005 12/1959 France .
2379280 9/1978 France .
52-139732 11/1977 Japan .
54-138134 10/1979 Japan .
55-28930 2/1980 Japan .
55-83708 6/1980 Japan .
60-16910 1/1985 Japan .

OTHER PUBLICATIONS

Chemical Abstracts, vol. 99, No. 24, Dec. 1983, p. 326, Abstract No. 200348a.
Chemical Abstacts, vol. 94, No. 8, Feb. 1981, p. 354, Abstract No. 52703s.
Remz, *Cosmetics and Toiletries,* vol. 103, 70 Dec. (1988).

*Primary Examiner*—Thurman K. Page
*Assistant Examiner*—William E. Benston, Jr.
*Attorney, Agent, or Firm*—Sprung Horn Kramer & Woods

[57] ABSTRACT

A solvent type nail enamel composition comprising (i) a silicone resin having the average composition formula (I):

$$R_a SiO_{(4-a)/2} \qquad (I)$$

wherein R represents a substituted or unsubstituted monovalent hydrocarbon group and a represents a positive number of $0.8 < a < 1.8$, and (ii) a cellulose derivative; a solvent type nail enamel composition wherein the silicone resin has a molecular weight of 250 to 100,000; and a solvent type nail enamel composition wherein the amounts of the silicone resin and the cellulose derivative in the composition are 1% to 50% by weight and 0.5% to 15.0% by weight, respectively.

3 Claims, No Drawings

SOLVENT TYPE NAIL ENAMEL COMPOSITION

BACKGROUND OF THE INVENTION

1. Field of the Invention

The present invention relates to a solvent type nail enamel composition. More specifically, it relates to a solvent type nail enamel composition containing a special silicone resin and a cellulose derivative.

The term, solvent nail enamel, of the present invention, also includes a base coat, a top coat used for improving the luster and durability of a nail enamel or an emulsified enamel formulated with water.

2. Description of the Related Art

Solvent type nail enamels of the prior art comprise nitrocellulose, a resin such as an alkyd type resin, acrylic type resin, toluenesulfonamide type resin, and sucrose benzoic acid ester resin, a plasticizer and a solvent, as the main base components, formulated together, if necessary, with a pigment, a dye, or a pearl agent. The above-mentioned solvent type nail enamels are widely used because they provide an excellent and easy coating thereof on a nail, a good luster and a good durability, but since a solvent such as butyl acetate or toluene is an essential component thereof, the solvent is very slow to evaporate and thus a problem arises with a dryability of the nail enamel. Also, since the film forming agent consists of nitrocellulose as the main skeleton, a drawback common among solvent type nail enamels is a feeling of pressure on the finger tips after drying.

Various studies have been made in an attempt to solve these problems. For example, to enhance the dryability of the nail enamel, attempts have been made to use acetone and methyl ethyl ketone, which are rapidly evaporating, low boiling solvents, as the solvent, but although the dryability is improved, the ease of coating the nail is lost, and thus a uniform coating cannot be applied. Also, opposing characteristics exist such that damage to the nail cannot be avoided, thus failing to solve the above problems. For the feeling of pressure on the nail after drying, a "Manicure Agent Having Oxygen Gas Permeability" proposed by Japanese Patent Publication (Kokoku) No. 62-40322 is known, which comprises a silicone resin or a silicone type copolymer having an oxygen gas permeability formulated therein, and is characterized by a good film forming property, a satisfactory feeling at the finger tips after coating, and no damage to the nail after use over a long period. Nevertheless, the above-mentioned manicure agent is extremely unsatisfactory from the viewpoints of luster, durability and dryability, and thus lacks the basic functions required of a manicure agent.

SUMMARY OF THE INVENTION

Accordingly, the objects of the present invention are to eliminate the above-mentioned disadvantages of the prior art and to provide a nail enamel having an excellent luster and durability, and a rapid drying rate, which does not apply a feeling of pressure to the finger tips.

Other objects and advantages of the present invention will be apparent from the following description.

In accordance with the present invention, there is provided a solvent type nail enamel composition comprising;

(i) a silicone resin having the average composition formula (I):

$$R_aSiO_{(4-a)/2} \qquad (I)$$

wherein R represents a substituted or unsubstituted monovalent hydrocarbon group and a represent a positive number of $0.8 < a < 1.8$, and (ii) a cellulose derivative In accordance with the present invention, there is also provided a solvent type nail enamel composition comprising the above-mentioned silicone resin (I) and 11 to 25% by weight of nitrocellulose.

In accordance with the present invention, there is further provided a solvent type nail enamel composition comprising the above-mentioned silicone resin (I) and 25 to 50% by weight of a highly volatile solvent.

In accordance with the present invention, there is further provided a solvent type nail enamel composition comprising the above-mentioned silicone resin (I), 11 to 25% by weight of nitrocellulose and 25 to 50% by weight of a highly volatile solvent.

DESCRIPTION OF THE PREFERRED EMBODIMENTS

The silicone resin usable in the solvent type nail enamel composition of the present invention is represented by the formula (I)

$$R_aSiO_{(4-a)/2} \qquad (I)$$

wherein R represents a substituted or unsubstituted monovalent hydrocarbon group, and a represents a positive number of $0.8 < a < 1.8$. Specific examples of R in the formula (I) include substituted or unsubstituted monovalent hydrocarbon groups having 1 to 10 carbon atoms, and typical examples are alkyl groups such as methyl, ethyl, propyl and the like; alkenyl groups such as vinyl, allyl, hexenyl and the like; cycloalkyl groups such as cyclohexyl, cyclohepthyl and the like; aryl groups such as phenyl, tolyl, xylyl and the like; aralkyl groups such as benzyl, phenylethyl and the like; halogen-substituted monovalent hydrocarbon groups such as chlorophenyl, tetrachlorophenyl, chloromethyl, pentafluorobutyl, trifluoropropyl and the like; and alternatively, γ-glycidoxy group, β-(3,4-epoxycyclohexyl) group, cyanoethyl group, γ-aminopropyl group, and N-β-(aminoethyl)-γ-aminopropyl group. One or more compounds can be chosen from among the above, but those of the methyl group and phenyl group are most preferred.

The number of organic groups directly bonded to these silicons is 0.8 to 1.8, on an average, per silicon atom, preferably 1.0 to 1.5. When this number is less than 0.8, the enamel composition is hard and brittle and cannot follow a bending of the nail, and thus the durability is worsened. On the other hand, when this number exceeds 1.8, the drying rate is slow and the film becomes sticky. The amount of the formulated silicone resin usable in the present invention is preferably 1 to 50% by weight, more preferably 5 to 30% by weight, based on the total amount of the solvent type nail enamel composition. When this amount is less than 1.0% by weight, the luster, drying and feeling of pressure are poor, and when this amount is more than 50.0% by weight, the durability is worsened.

The above-mentioned silicone resins can be prepared by known methods. Namely, after a silane represented by:

$$R_bSiX_{4-b}$$

wherein R is the same as defined above, b is a number of 0 to 3, X is a hydrolyzable group is formulated at the ratio corresponding to the siloxane structure, the formulated product is hydrolyzed by a conventional procedure, and a polymerization is then carried out to prepare the desired polymer.

In the selection of the silane, a variety of combinations may be conceived and used within the range of the above-mentioned average formula, but the combination of $R_2SiX_2$ and $RSiX_3$ is most preferable.

The polymerization degree of the silicone resin usable in the present invention is preferably within the range of a molecular weight of from 250 to 100,000. When a polymerization degree is lower than this range, the drying rate is slow, and at a degree higher than this range, the compatibility, if any, with a cellulose derivative is poor and a coating having a pleasing appearance cannot be obtained.

Also, remaining silanol groups ($\equiv SiOH$), e.g., groups formed by hydrolysis and hydrolyzable groups X such as an alkoxy group, are also included within the category of the present invention.

The cellulose derivatives usable in the first embodiment of the present invention are those obtained by substituting a part or all of the hydroxyl groups in the cellulose with other organic groups. Examples of such as celluloses are methyl cellulose, ethyl cellulose, propyl cellulose, butyl cellulose, acetyl cellulose, nitrocellulose, cellulose phthalate, hydroxyethyl cellulose, hydroxy propyl cellulose, cellulose acetate propionate, cellulose acetate butyrate, cellulose acetate, and phthalate. Among the above, ethyl cellulose and cellulose acetate butyrate are most preferable. The amount of formulated cellulose in the present invention is preferably 0.5 to 15.0% by weight, more preferably 1.5 to 5.0% by weight, of the total amount of the nail enamel composition. When this amount is less than 0.5% by weight or more than 15.0% by weight, the durability is worsened in both cases.

In the first embodiment of the present invention, there may be used, as a solvent, aromatic hydrocarbons such as toluene, xylene and the like, ester type solvents such as n-butyl acetate, isobutyl acetate and the like, alcohol type solvents such as butanol, isopropanol and the like, ketone type solvents such as methyl ethyl ketone, methyl isobutyl ketone and the like, ether type solvents such as cellsolve, carbitol and the like, and branched saturated hydrocarbons such as Isopar G, and H. These are not limitative of the present invention, and acetone also can be formulated at a level which does not cause damage to the nails. One or more kinds of these solvents can be formulated, and the amount formulated is preferably 50 to 85% by weight of the total amount of the nail enamel.

In the solvent type nail enamel composition according to the first embodiment of the present invention, nitrocellulose, resins other than silicone resins, plasticizers, and pigments can be formulated in addition to the above-mentioned components.

Examples of the nitrocellulose are nitrocellulose RS ¼ sec., nitrocellulose RS ½ sec., nitrocellulose SS ¼ sec., nitrocellulose SS ½ sec., nitrocellulose HIG ¼ sec., nitrocellulose HIG ½ sec., and nitrocellulose SL-1. The amount formulated if any, is preferably 5 to 25% by weight of the total amount of the nail enamel composition.

Examples of resins other than the above-mentioned silicone resin are synthetic resins such as an alkyd type resin, acrylic type resin, toluenesulfonamide type resin, and sucrose benzoic acid ester type resin, or natural resins such as rosin and shellac. The amount formulated is preferably 3 to 15% by weight of the total amount of the nail enamel composition.

Examples of the plasticizer are a phthalic acid ester type such as dibutyl phthalate or dioctyl phthalate, an citric acid ester type such as tributyl citrate, acetyltributyl citrate, and acetyltriethyl citrate, and others. The amount formulated is preferably 0.1 to 8.0% by weight of the total amount of the nail enamel composition.

Examples of the pigment are inorganic pigments such as iron oxide (red), iron oxide (yellow), iron oxide (black), and titanium oxide, organic pigments such as yellow No. 4, Red No. 226, Red No. 202, and Red No. 204, and others. The amount formulated is preferably 5.0% by weight of the total amount of the nail enamel.

Examples of the nitrocellulose usable in the second and fourth embodiments of the present invention include nitrocellulose RS ¼ sec., nitrocellulose RS ½ sec., nitrocellulose SS ¼ sec., nitrocellulose SS ½ sec., nitrocellulose HIG ¼ sec., nitrocellulose HIG ½ sec., and nitrocellulose SL-1. The amount formulated is preferably 11 to 25% by weight, more preferably 13 to 20% by weight, of the total amount of the nail enamel. If this amount is less than 11% by weight, the enamel is liable to be peeled off, and if this amount is more than 25% by weight, the coating of the enamel becomes difficult.

Examples of the highly volatile solvent usable in the third and fourth embodiment of the present invention are aromatic hydrocarbons such as toluene, xylene and the like, ethyl acetate, alcohol type solvents such as isopropanol and the like, ketone type solvents such as methyl ethyl ketone, methyl isobutyl ketone and the like, branched saturated hydrocarbons such as Isopar G, H. These are not limitative of the present invention, and acetone can be formulated at a level which does not cause damage to the nail. One or more kinds of these solvents can be formulated, and the amount formulated is preferably 25 to 50% by weight, more preferably 30 to 40% by weight, of the total amount of the nail enamel composition. When the amount is less than 25% by weight, the drying rate is slow, and when more than 50% by weight, the coating becomes difficult.

In the solvent type nail enamel composition of the second, third, and fourth embodiments of the present invention, the above-mentioned resins other than silicone resins, plasticizers, and pigments also can be formulated.

In the solvent type nail enamel of the present invention, there may be also formulated, if necessary, perfumes, dyes, lamellar agents, drugs, humectants, UV-ray absorbers, matte agents, fillers, surfactants, and metal soaps. Note, these must be used under qualitative and quantative conditions which do not impair the effect of the present invention.

The solvent type nail enamel of the present invention is an epoch-making solvent type nail enamel having a superior ease of coating, luster, durability, and drying rate, and does not give a feeling of pressure at the finger tips, and thus has solved the problems of conventional nail enamels.

EXAMPLES

The present invention will now be further illustrated in detail by, but is by no means limited to, the following Examples, wherein the amounts formulated are in % by weight. Before describing the Examples, the effect testing methods and evaluation methods of the present invention are shown below.

| | |
|---|---|
| Easiness of coating | |
| Evaluated organoleptically in practical use. | |
| Very easy to coat | ++ |
| Relatively easy to coat | + |
| Slightly difficult to coat | ± |
| Difficult to coat | − |
| Very difficult to coat | −− |
| Luster | |
| Organoleptically evaluated in practical use. | |
| Very high luster | ++ |
| Some luster | + |
| Slight luster | ± |
| Little luster | − |
| No luster at all | −− |
| Drying rate | |
| In practical use, the time immediately after coating until the time at which the finger is not adhered thereto when the enamel is touched is measured. | |
| 1–2 min | ++ |
| 2–3 min | + |
| 3–4 min | ± |
| 4–6 min | − |
| 6 min. or longer | −− |
| Feeling of pressure at finger tips | |
| Organoleptically evaluated in practical use. | |
| No feeling of pressure | ++ |
| Slight feeling of pressure | + |
| Little feeling of pressure | ± |
| Feeling of pressure | − |
| Durability | |
| Strong feeling of pressure | −− |
| Organoleptically evaluated in practical use. | |
| Very difficult to peel | ++ |
| Slightly difficult to peel | + |
| Rather easily peeled | ± |
| Easily peeled | − |
| Very easily peeled | −− |

EXAMPLE 1 AND COMPARATIVE EXAMPLES 1 AND 2

Nail enamels were prepared according to the recipes shown in Table 1, and the qualities thereof were evaluated.

TABLE 1

| | (% by weight) | | |
|---|---|---|---|
| | Example 1 | Comp. Ex. 1 | Comp. Ex. 2 |
| (1) Nitrocellulose RS1/4 sec. | 10.0 | 14.0 | 14.0 |
| (2) Alkyd resin | 8.0 | 16.0 | 16.0 |
| (3) Dibutyl phthalate | 5.0 | 5.0 | 5.0 |
| (4) Ethyl acetate | 20.0 | 20.0 | 20.0 |
| (5) n-Butyl acetate | 31.0 | 37.0 | 17.0 |
| (6) Ethyl alcohol | 8.0 | 8.0 | 8.0 |
| (7) Acetone | — | — | 20.0 |
| (8) Pigment | q.s. | q.s. | q.s. |
| (9) Organic bentonite thickener | q.s. | q.s. | q.s. |
| (10) Silicone resin ($R_{1.2}SiO_{1.4}$, R: phenyl/methyl = 2.5 (mol ratio), M.W. 3000 | 15.0 | — | — |
| (11) Ethyl cellulose | 3.0 | — | — |
| Ease of coating | ++ | ++ | − |
| Luster | ++ | ++ | ± |
| Drying rate | ++ | −− | ++ |
| Feeling of pressure at finger tips | ++ | − | − |
| Durability | ++ | ++ | ++ |

(Preparation method)

In (4) to (7) were dissolved (1) to (3) and (10) and (11), followed by mixing with (8) and (9) while stirring, to prepare samples.

As apparent from Table 1, Example 1 provides superior characteristics of ease of coating, luster, dryability, feeling of pressure at the finger tips, and durability. In contrast, it can be understood that Comparative Example 1 of a conventional type in which silicone resin and ethyl cellulose is not formulated has an inferior drying rate, and gives a strong feeling of pressure at the finger tips, and Comparative Example 2, in which acetone is formulated, gives a markedly strong feeling of pressure at the finger tips.

EXAMPLES 2–4 AND COMPARATIVE EXAMPLES 3–12

Nail enamels were prepared according to the recipes shown in Table 2, and the qualities thereof were evaluated.

TABLE 2

| | (% by weight) | | | | | | | | | | | | |
|---|---|---|---|---|---|---|---|---|---|---|---|---|---|
| | Example | | | Comparative Example | | | | | | | | | |
| | 2 | 3 | 4 | 3 | 4 | 5 | 6 | 7 | 8 | 9 | 10 | 11 | 12 |
| Nitrocellulose RS 1/4 sec. | 10.0 | 10.0 | 10.0 | 10.0 | 14.0 | 10.0 | 10.0 | 10.0 | 10.0 | 10.0 | 10.0 | 10.0 | 10.0 |
| Alkyd resin | 10.0 | 10.0 | 10.0 | 10.0 | 16.0 | 10.0 | 10.0 | 10.0 | 10.0 | 10.0 | 10.0 | 10.0 | 10.0 |
| Acetyltributyl citrate | 5.0 | 5.0 | 5.0 | 5.0 | 5.0 | 5.0 | 5.0 | 5.0 | 5.0 | 5.0 | 5.0 | 5.0 | 5.0 |
| Ethyl acetate | 20.0 | 20.0 | 10.0 | 20.0 | 20.0 | 20.0 | 20.0 | 20.0 | 20.0 | 20.0 | 12.0 | 20.0 | 20.0 |
| n-butyl acetate | 34.0 | 31.0 | 9.0 | 32.0 | 34.0 | 29.0 | 29.0 | 29.0 | 29.0 | 43.5 | — | 31.95 | 15.0 |
| Isopropyl alcohol | 8.0 | 8.0 | 8.0 | 8.0 | 8.0 | 8.0 | 8.0 | 8.0 | 8.0 | 8.0 | 8.0 | 8.0 | 8.0 |
| Pigment | q.s. | q.s. | q.s. | q.s. | q.s. | q.s. | q.s. | q.s. | q.s. | q.s. | q.s. | q.s. | q.s. |
| Organic bentonite thickener | q.s. | q.s. | q.s. | q.s. | q.s. | q.s. | q.s. | q.s. | q.s. | q.s. | q.s. | q.s. | q.s. |
| Silicone resin | 10.0 | 1.50 | 45.0 | 15.0 | — | 15.0 | 15.0 | 15.0 | 15.0 | 0.5 | 52.0 | 15.0 | 15.0 |
| "a" in $RaSiO_{(4-a)/2}$ | 1.0 | 1.8 | 1.3 | 1.3 | — | 0.7 | 2.0 | 1.3 | 1.3 | 1.3 | 1.3 | 1.3 | 1.3 |
| R: Phenyl/methyl (mol ratio) | 2.5 | 0.8 | 1.0 | 1.0 | 1.0 | 1.0 | 1.0 | 1.0 | 0.5 | 1.0 | 1.0 | 1.0 | 1.0 |
| M.W. | 250 | 100000 | 3000 | 3000 | — | 3000 | 3000 | 200 | 150000 | 3000 | 3000 | 3000 | 3000 |
| Cellulose acetate butyrate | 3.0 | 1.0 | 3.0 | — | 3.0 | 3.0 | 3.0 | 3.0 | 3.0 | 3.0 | 3.0 | 0.05 | 17.0 |
| Ease of coating | ++ | + | + | ++ | ++ | ++ | ++ | ++ | ++ | ± | ++ | ++ | ++ |
| Luster | ++ | ++ | ++ | + | + | ++ | ++ | ++ | | + | ++ | ++ | ++ |
| Drying rate | ++ | ++ | ++ | ± | −− | ++ | ± | −− | | −− | ++ | − | ++ |
| Feeling of pressure at finger tips | ++ | ++ | ++ | ++ | − | ++ | ++ | ++ | | − | ++ | ++ | ++ |
| Durability | ++ | ++ | + | ± | + | −− | −− | ++ | | ++ | − | − | − |

As apparent from Table 2, Examples 2 to 4 show excellent characteristics of ease of coating, luster, drying rate, feeling of pressure at the finger tips, and durability. Comparative Example 3 is a system in which no cellulose derivative was formulated, and has a poor drying rate and durability. Comparative Example 4 is a system in which no silicone resin was formulated, and has a markedly unsatisfactory drying rate and high feeling of pressure at the finger tips. Comparative Example 5 is the case where a is equal to 0.5 in the average composition formula $R_aSiO_{(4-a)/2}$, and the film is brittle with a markedly impaired durability. Comparative Example 6 is the case where a is equal to 2.0 in the average composition formula $R_aSiO_{(4-a)/2}$, and the drying rate is lowered and the durability is worsened. Comparative Example 7, which is the case where the molecular weight of the silicone resin is remarkably small (MW=200), has a very poor drying rate. On the contrary, Comparative Example 8, which is the case where the molecular weight is 150,000, has a poor compatibility with the cellulose derivative, and thus a good coating can not be obtained and the respective characteristic evaluations are not good. Comparative Example 9 is the case of the formulation where the silicone resin is contained in an extremely small amount, and gives a poor drying rate and strong feeling of pressure at the finger tips. Comparative Example 10 is the case where the silicone resin is contained in a large amount, and thus the durability is poor. Comparative Examples 11, 12 are the cases where the amounts of cellulose acetate butyrate formulated are very large and very small; Comparative Example 11 has a poor drying rate and durability, and Comparative Example 12 also has a poor durability.

As apparent from the above results, the solvent type nail enamel of the present invention is an epoch-making solvent type nail enamel having a superior ease of coating, high luster, good drying rate, and good durability, and does not provide a feeling of pressure at the finger tips.

EXAMPLE 5

Transparent Type Nail Enamel

A transparent nail enamel composition was prepared by a conventional procedure.

| | |
|---|---|
| Nitrocellulose HIG 1/4 | 18.0% by weight |
| Acrylic resin | 10.0 |
| Acetyl tributyl citrate | 5.0 |
| Ethyl acetate | 20.0 |
| n-Butyl acetate | 14.0 |
| Ethyl alcohol | 8.0 |
| Silicone resin | 20.0 |
| $R_aSiO_{(4-a)/2}$, R:phenyl/methyl = 1.5 (mol ratio), a = 1.0, MW = 3000 | |
| Cellulose acetate butyrate | 5.0 |

The transparent type nail enamel of Example 5 was found to have a superior ease of coating, luster, drying rate, no feeling of pressure at the finger tips, and a good durability.

EXAMPLES 6-8 AND COMPARATIVE EXAMPLES 13-15

Nail enamels were prepared according to the recipes shown in Table 3, and the qualities thereof were evaluated.

TABLE 3

| | (% by weight) | | | | | |
|---|---|---|---|---|---|---|
| | Comparative Example | | | Example | | |
| | 13 | 14 | 15 | 6 | 7 | 8 |
| (1) Nitrocellulose RS1/4 sec. | 18.0 | 11.0 | 11.0 | 17.0 | 10.0 | 17.0 |
| (2) Alkyd resin | 8.0 | 8.0 | 8.0 | 5.0 | 5.0 | 5.0 |
| (3) Dibutyl phthalate | 5.0 | 5.0 | 5.0 | 5.0 | 5.0 | 5.0 |
| (4) Ethyl acetate | 20.0 | 25.0 | 25.0 | 20.0 | 40.0 | 40.0 |
| (5) n-Butyl acetate | 41.0 | 38.0 | 38.0 | 40.0 | 27.0 | 20.0 |
| (6) Ethyl alcohol | 8.0 | 8.0 | 8.0 | 8.0 | 8.0 | 8.0 |
| (7) Acetone | q.s. | q.s. | q s. | q.s. | q.s. | q.s. |
| (8) Pigment | q.s. | q.s. | q.s. | q.s. | q.s. | q.s. |
| (9) Silicone resin | — | 5.0 | 5.0 | 5.0 | 5.0 | 5.0 |
| "a" in $R_a SiO_{(4-a)/2}$ R: Phenyl/methyl = 2.5 (mol ratio), M.W. 3000 | — | 0.3 | 3.0 | 1.2 | 1.2 | 1.2 |
| Ease of coating | ++ | ++ | ++ | ++ | ++ | ++ |
| Luster | + | + | −− | ++ | ++ | ++ |
| Drying rate | − | ± | −− | ± | ++ | ++ |
| Feeling of pressure at finger tips | −− | ++ | ++ | ++ | ++ | ++ |
| Durability | + | −− | −− | ++ | ± | ++ |

(Preparation method)

In (4) to (7) were dissolved (1) to (3) and (9), followed by mixing with (7) and (8) while stirring, to prepare samples.

As apparent from Table 3, Examples 6 to 8 provide superior characteristics of ease of coating, luster, dryability, feeling of pressure at the finger tips, and durability.

In contrast, it can be understood that Comparative Example 13, in which no silicone resin is formulated, has a markedly poor drying rate, strong feeling of pressure at the finger tips, and the enamel of Comparative Example 14, in which a silicone resin with a small a is employed, has a very poor durability. Also, it can be understood that Comparative Example 15 in the case of too great an a has a markedly poor luster, drying rate, and durability.

As apparent from the results described above, the solvent type nail enamel of the present invention is an epoch-making creation having a superior ease of coating, luster, drying rate, and durability, and does not give a feeling of pressure at the finger tips.

EXAMPLE 9

Solvent Type Nail Enamel

A solvent type nail enamel was prepared by a conventional procedure.

| | |
|---|---|
| Nitrocellulose HIG 1/4 | 11.0% by weight |
| Acrylic resin | 5.0 |
| Acetyl tributyl citrate | 5.0 |
| Ethyl acetate | 25.0 |
| n-Butyl acetate | 36.0 |
| Ethyl alcohol | 8.0 |
| Pigment | q.s. |
| Organic bentonite type thickener | q.s. |
| Silicone resin | 10.0 |
| $R_{0.9}SiO_{1.55}$, R: Phenyl/methyl = 2.5 (mol ratio), molecular weight 3,000 | |

EXAMPLE 10

Solvent Type Nail Enamel

A solvent type nail enamel was prepared by a conventional procedure.

| | |
|---|---|
| Nitrocellulose HIG 1/4 | 25.0% by weight |
| Acrylic resin | 5.0 |
| Acetyl tributyl citrate | 5.0 |
| Ethyl acetate | 50.0 |
| n-Butyl acetate | 18.0 |
| Ethyl alcohol | 8.0 |
| Pigment | q.s. |
| Organic bentonite type thickener | q.s. |
| Silicone resin | 10.0 |
| $R_{0.7}SiO_{1.15}$, R: phenyl/methyl = 2.5 (mol ratio), molecular weight 3,000 | |

EXAMPLE 11

Transparent Type Nail Enamel

A transparent type nail enamel was prepared by a conventional procedure.

| | |
|---|---|
| Nitrocellulose HIG 1/4 | 18.0% by weight |
| Acrylic resin | 10.0 |
| Acetyl tributyl citrate | 5.0 |
| Ethyl acetate | 10.0 |
| n-Butyl acetate | 17.0 |
| Ethyl alcohol | 5.0 |
| *-continued* | |
| Silicone resin | 5.0 |
| $R_aSiO_{(4-1)/2}$, R: phenyl/methyl = 1.5 (mol ratio), molecular weight 3,000 | |

The nail enamels of Examples 9, 10, and 11 were found to have a superior ease of coating, luster, drying rate, no feeling of pressure at the finger tips, and a good durability.

We claim:

1. A solvent nail enamel composition comprising:
   (i) 1% to 50% by weight of a silicone resin having a molecular weight of 250 to 100,000 and having the average composition formula (I):

$$R_aSiO_{(4-a)/2} \qquad (I)$$

wherein R represents a substituted or unsubstituted monovalent hydrocarbon group, and a represents a positive number of $0.8 < a < 1.8$,
   (ii) 11 to 25% by weight of nitrocellulose; and
   (iii) 25 to 50% by weight of a highly volatile solvent.

2. A solvent type nail enamel composition as claimed in claim 1, wherein the amount of silicone resin is 5 to 30% by weight based upon the total amount of the composition.

3. A solvent nail enamel composition as claimed in claim 1, wherein the amounts of the silicone resin and the cellulose derivative in the composition are 5% to 30% by weight and 1.5% to 5.0% by weight, respectively.

* * * * *

UNITED STATES PATENT AND TRADEMARK OFFICE
CERTIFICATE OF CORRECTION

PATENT NO. : 5,225,195
DATED : July 6, 1993
INVENTOR(S) : Soyama et al.

It is certified that error appears in the above-identified patent and that said Letters Patent is hereby corrected as shown below:

Col. 10, claim 2   After " solvent " delete " type "
line 1

Signed and Sealed this

Seventh Day of June, 1994

Attest:

BRUCE LEHMAN

*Attesting Officer*         Commissioner of Patents and Trademarks

UNITED STATES PATENT AND TRADEMARK OFFICE
CERTIFICATE OF CORRECTION

PATENT NO. : 5,225,195
DATED : July 6, 1993
INVENTOR(S) : Soyama, et al

It is certified that error appears in the above-indentified patent and that said Letters Patent is hereby corrected as shown below:

On the title page, item [73] Assignee: After "Shiseido Company Ltd.," insert --Shin-Etsu Chemical Company Ltd.,--

Signed and Sealed this

Twenty-first Day of February, 1995

Attest:

BRUCE LEHMAN

Attesting Officer          Commissioner of Patents and Trademarks